United States Patent [19]

Lee et al.

[11] Patent Number: 4,665,268

[45] Date of Patent: May 12, 1987

[54] CATALYTIC CONVERSION OF METHANOL TO LIGHT OLEFINS

[75] Inventors: Carol S. Lee, Princeton; George E. Stead, Kendall Park, both of N.J.

[73] Assignee: Mobil Oil Corporation, New York, N.Y.

[21] Appl. No.: 879,788

[22] Filed: Jun. 27, 1986

Related U.S. Application Data

[63] Continuation-in-part of Ser. No. 429,933, Sep. 30, 1982, abandoned.

[51] Int. Cl.[4] .............................................. C07C 1/20
[52] U.S. Cl. ..................................... 585/640; 585/733
[58] Field of Search ......................................... 585/640

[56] References Cited

U.S. PATENT DOCUMENTS

| | | | |
|---|---|---|---|
| 4,025,575 | 5/1977 | Chang et al. | 260/682 |
| 4,049,573 | 9/1977 | Kaeding | 252/432 |
| 4,083,889 | 4/1978 | Caesar et al. | 260/682 |
| 4,088,706 | 5/1978 | Kaeding | 260/668 R |
| 4,247,731 | 1/1981 | Wunder et al. | 585/640 |
| 4,278,565 | 7/1981 | Chen et al. | 585/640 |
| 4,296,266 | 10/1981 | Wunder et al. | 585/640 |

Primary Examiner—Curtis R. Davis
Attorney, Agent, or Firm—A. J. McKillop; M. G. Gilman; E. F. Kenehan, Jr.

[57] ABSTRACT

A process is disclosed for converting a methanol-containing feed to a light olefin-containing product over a ZSM-12 zeolite catalyst, preferably modified by incorporation of either magnesium, manganese or both magnesium and manganese. By using such Mg and/or Mn-modified ZSM-12 zeolite catalysts, methanol and/or methyl ether can be converted to an olefin-containing hydrocarbon product enriched in $C_2$ to $C_4$ olefins and especially enriched in the particular light olefin propylene.

13 Claims, No Drawings

CATALYTIC CONVERSION OF METHANOL TO LIGHT OLEFINS

CROSS-REFERENCE TO RELATED APPLICATION

This application is a continuation-in-part of copending U.S. application Ser. No. 429,933, filed Sept. 30, 1982 now abandoned, the entire disclosure of which is expressly incorporated herein by reference.

BACKGROUND OF THE INVENTION

1. Field of the Invention

This invention relates to an improved process for converting a methanol feed to light olefins over modified crystalline aluminosilicate zeolite catalysts.

2. Description of the Prior Art

A remarkable growth in the production of synthetic fibers, plastics and rubber has taken place in recent decades. Such growth, to a large extent, has been supported and encouraged by an expanding supply of inexpensive petroleum raw materials such as ethylene and propylene. However, increasing demand for these light olefins has, from time to toime, led to periods of shortage, either due to a diminished supply of suitable feedstocks or to limited processing capacity. In any event, it is now considered highly desirable to provide efficient means for converting raw materials other than petroleum to light olefins.

One such non-petroleum source of light olefins is coal-derived methanol. In this respect, it is known that methanol can be catalytically converted to olefin-containing hydrocarbon mixtures by contact under certain conditions with particular types of crystalline zeolite catalysts materials. U.S. Pat. No. 4,025,575, issued May 24, 1977, to Chang et al and U.S. Pat. No. 4,083,889, issued Apr. 11, 1978 to Ceaser et al, for example, both disclose processes whereby methanol and/or methyl ether can be converted to an olefin-containing product over a ZSM-5 type (Constraint Index 1–12) zeolite catalyst. ZSM-5, in fact, converts methanol and/or methyl ether to hydrocarbons containing a relatively high concentration of light ($C_2$ and $C_3$) olefins.

Modification of zeolite methanol conversion catalysts with, for instance, silica, phosphorus, metal ions or metal oxides, can enhance selectively of the methanol conversion reaction for production of light olefins. For example, Wunder et al.; U.S. Pat. No. 4,247,731; Issued Jan. 27, 1981 and Wunder et al.; U.S. Pat. No. 4,296,266; Issued Oct. 20, 1981, both disclose modification of zeolites such as Zeolite X with manganese and optionally with additional materials such as magnesium in order to enhance ethylene selectively of such zeolites when they are used to catalyze methanol/dimethyl ether conversion.

It is also known that light olefin, and especially ethylene, production from the catalytic conversion of methanol can be optimized by varying one or more reaction parameters. Variations in reaction temperature, pressure and reactant space velocity can, for example, alter the selectivity of the methanol conversion reaction to produce different kinds of hydrocarbon products, e.g. to maximize light olefin production.

Likewise, utilization of dilute methanol feeds or inert diluents can also tend to increase selectivity of the reaction toward ethylene and light olefin production. Notwithstanding the existence of process suitable for converting methanol to high yields of light olefins, there is a continuing need to develop additional catalytic procedures suitable for converting an organic charge comprising methanol to light olefin products with improved light olefin selectivity and especially with improved selectivity to propylene, which, like ethylene, is a valuable feedstock material.

Accordingly, it is an object of the present invention to provide an improved process for converting a methanol feed to olefin-containing products with high selectivity to production of propylene.

It is a further object of the present invention to provide such a selective methanol conversion process which can be employed in conjunction with known catalysts and processes for maximizing light olefin product from methanol.

It is a further object of the present invention to provide such a selective methanol conversion process employing conventional catalysts, readily available reactants and diluents and commercially practical reaction conditions.

SUMMARY OF THE INVENTION

In accordance with the present invention, a process is provided for the catalytic conversion of a methanol-containing feed to a hydrocarbon mixture containing light olefins. The catalyst employed in such a process comprises at least some crystalline aluminosilicate zeolite material of the ZSM-12 type. This ZSM-12 zeolite is modified by incorporation therein of a minor proportion of a catalyst modifier which can be magnesium, manganese or a combination of both magnesium and manganese. Methanol conversion over such a modified ZSM-12 catalyst occurs under conversion conditions which are sufficient to thereby produce a light olefin-containing product enriched in propylene.

DETAILED DESCRIPTION OF THE INVENTION

In accordance with the present invention, a methanol containing feed is catalytically converted to an olefin containing hydrocarbon product. The term "methanol-containing feed" as used herein can comprise both the organic material used as reactants, i.e. the organic compounds such as methanol and methyl ether subjected to catalytic conversion to olefins, as well as additional components such as water or other diluents. Since methanol is miscible with water, the charge to the catalytic reaction zone may actually contain relatively large amounts of water, but only the methanol, and associated organic compounds, constitute the reaction portion of the methanol-containing feed.

Any methanol product comprising at least 60 wt. % of methanol may be used to provide methanol for the methanol-containing feed in this invention. Substantially pure methanol, such as industrial grade anhydrous methanol, is eminently suitable. Crude methanol, which usually contains from 12 to 30 wt. % water, or more dilute solutions, also may be used.

Small amounts of impurities such as higher alcohols, aldehydes, or other oxygenated compounds in the methanol-containing feed have little effect on the conversion reaction of this invention. The methanol-containing feed may include methyl ether. When this component is present, it can comprise up to 100% of the "methanol-containing feed," but it is preferred that methyl ether constitute not more than about 20 wt. % of the total methanol-containing feed. For purposes of the present invention, it is contemplated to directly convert methanol and/or methyl ether in the feed to a hydrocarbon mixture characterized by a high content of light olefins, especially propylene. Such amounts of methyl ether as may be formed concomitantly in the conversion reaction, however, may be recovered and recycled with fresh methanol feed, and the methyl ether content calculated on the total of recycle and fresh feed preferably will not exceed the above-noted 20 wt. %.

In one embodiment of the present invention, the charge to the reaction zone comprises only the methanol and associated organic oxygenates. In another preferred embodiment of the present process, selectivity of the methanol conversion reaction for production of light ($C_2$-$C_3$) olefins can be increased by contacting methanol feed with the hereinafter described modified zeolite based catalyst in the presence of up to about 20 mols, and preferably from about 1 to 10 mols of steam per mol of methanol feed. Such steam contact is made in the reaction zone under the methanol conversion conditions hereinafter described. Such steam may be provided directly by injecting the requisite amount of water or steam into the reaction zone. Alternatively, steam may be provided totally or in part by water present in the methanol-containing feed in a molar ratio of water to methanol of up to about 20:1, preferably from about 1:1 to 10:1. Such water in the charge to the reaction zone, of course, forms steam in the reaction zone under the conversion conditions of the present invention.

The methanol-containing feed as hereinbefore described is catalytically converted to a light olefin containing hydrocarbon product enriched in propylene by contact with a modified catalyst comprising a particular type of crystalline aluminosilicate zeolite material known as ZSM-12.

Zeolite ZSM-12 is a member of a particular class of zeolitic materials which exhibit unusual properties. Although such zeolites have unusually low alumina contents, i.e. high silica to alumina mole ratios, they are very active when the silica to alumina mole ratio exceeds 30. The activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g., of the X and A type. Furthermore, carbonaceous deposits, when formed, may be removed by controlled burning at higher than usual temperatures to restore activity. These zeolites, used as catalysts, generally have low coke-forming activity and therefore are conducive to long times on stream between regenerations by controlled burning of carbonaceous deposits with oxygen-containing gas such as air.

An important characteristic of the crystal structure of this particular class of zeolites which includes ZSM-12 is that it provides a selective constrained access to and egress from the intracrystalline free space by virtue of having an effective poor size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the ZSM-12 zeolite crystal and to exclude aluminum in the binder or in cationic or other form within the channels. Although zeolites with a silica to alumina mole ratio of at least 12 are useful, it is preferred in some instances to use ZSM-12 zeolites having substantially higher silica/alumina ratios, e.g. 90:1 and above. In addition, ZSM-12 type zeolites as otherwise characterized herein but which are substantially free of aluminum, that is ZSM-12 zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful ZSM-12 zeolites described herein, that is to say those ZSM-12 zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

Zeolites of the particular class useful herein including ZSM-12 have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hour space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those ZSM-12 zeolites having a Constraint Index of about 1 to 12 and generally about 2. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those ZSM-12 zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites which includes ZSM-12 are those ZSM-12 zeolites which, when tested under two or more sets of conditions within the above-specified ranges of temperature and conversion, produce a value of the Constraint Index slightly less than 1, e.g., 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant zeolite definition whether or not the same identical zeolite, when tested under other of the defined conditions, may give a Constraint Index value outside of the range of 1 to 12.

ZSM-12 is descrbed in greater detail in U.S. Pat. No. 3,832,499 issued Aug. 27, 1974 to Rosinski and Rubin. The entire description contained within this patent, particularly the X-ray diffraction pattern of therein disclosed ZSM-12, is incorporated herein by reference.

In the ZSM-12 zeolite, the original cations can be subsequently replaced, at least in part, by calcination and/or ion exchange with another cation. Thus, the original cations can be exchanged into a hydrogen or hydrogen ion precursor form or a form in which the original cations have been replaced by a metal of, for example, Groups II through VIII of the Periodic Table. Thus, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing U.S. Pat. No. 3,832,449 to describe examples of specific members of the specified zeolite ZSM-12 calls with greater particularity, it is intended that identification of the therein disclosed crystalline zeolite ZSM-12 be resolved on the basis of its respective X-ray diffraction patterns. As discussed above, the present invention contemplates utilization of such catalysts wherein the mole ratio of silica to alumina is essentially unbounded. The incorporation of the identified patent should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline ZSM-12 zeolite material. Furthermore, the ZSM-12 zeolites of the present invention preferably have a crystal size of from about 0.02 to 0.5 micron.

The specific zeolite ZSM-12, when prepared in the presence of organic cations, is substantially catalytically inactive, possibly because the intra-crystalline free space is occupied by organic cations from the forming solution. The zeolite may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts and subsequently by treatment with magnesium and manganese salts as hereinafter described, followed by calcination in air at about 540° C. for from about 15 minutes to about 24 hours.

In a preferred aspect of this invention, the ZSM-12 zeolites herein are selected as those providing among other things a crystal framework density, in the dry hydrogen form, of not less than about 1.6 grams per cubic centimeter. It has been found that zeolites which satisfy all three of the discussed criteria are most desired for several reasons. Therefore, the preferred ZSM-12 zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including others besides the ZSM-12 utilized in this invention, are:

|  | Void Volume | Framework Denisty |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the ZSM-12 zeolite is conveniently converted to the ammonium form as a result of ammonium ion exchange. It is the ammonium form of ZSM-12 which is preferably employed as a precursor to the modified zeolites used in the process of the present invention.

The ZSM-12 zeolite used in the present invention preferably is characterized by an activity in terms of an alpha value of between about 25 and 250, and preferably between about 50 and 150. The alpha value reflects the relative activity of the catalyst with respect to a high activity silica-alumina cracking catalyst. To determine the alpha value, as such term is used herein, n-hexane conversion is determined at about 1000° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e. the silica-alumina standard. The silica-alumina reference catalyst contains about 10 weight percent $Al_2O_3$ and remainder $SiO_2$. This method of determining alpha is more fully described in the Journal of Catalysis, Vol. VI, Pages 278–287, 1966, incorporated herein by reference.

In practicing the methanol conversion process of the present invention, it may be useful to incorporate the above-described crystalline ZSM-12 zeolites with a matrix comprising another material resistant to the temperature and other conditions employed in the process. Such matrix material is useful as a binder and imparts greater resistance to the catalyst for the temperature, pressure and reactant feed stream velocity conditions which may be encountered in the methanol conversion process.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the ZSM-12 zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the from of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

As discussed more fully hereinafter, catalyst compositions comprising ZSM-12 zeolitic material as described above can be used to convert a methanol-containing charge to hydrocarbons. Such catalysts are especially useful in directing this conversion reaction toward light ($C_2$ to $C_4$) olefin production and especially toward the formation of propylene. In accordance with the present invention, it has been discovered that modification of such zeolites with particular divalent metals i.e., magnesium and/or manganese, can enhance the selectivity of such zeolite catalysts even further to the production of $C_2$–$C_4$ light olefins, and especially to production of propylene, during conversion of methanol and/or methyl ether to hydrocarbons.

The ZSM-12 zeolite catalysts herein are modified by incorporating thereon both a minor proportion of magnesium and/or a minor proportion of manganese. Such modified zeolite composites can be prepared by contacting the ZSM-12 zeolite composition with one or more compounds or complexes of the elements magnesium and/or manganese and by preferably thereafter heating the catalyst composite to convert the modifying elements to their oxide form. Incorporation can occur by the mechanisms of ion exchange, adsorption and/or impregnation, the latter two phenomena commonly being referred to as "stuffing." It should be emphasized that, while ion exchange can be used to incorporate the modifying metals onto the zeolite compositions described herein, ion exchange alone will generally not provide the requisite amount or form preferred (i.e. the oxide form) of incorporated magnesium and/or manganese onto the zeolite catalyst composites used in the present invention.

Generally, the zeolite composites of the present invention can be modified by contacting such composites with solutions of compounds of the magnesium and manganese metals to be incorporated. Such solutions may be formulated from any suitable solvent which is inert with respect to the metal-containing compound and the zeolite composition. Nonlimiting examples of some suitable solvents include water, aromatic and aliphatic hydrocarbons, alcohols, and organic acids (such as acetic acid, formic acid, propionic acid and so forth). Other commonly available solvents such as halogenated hydrocarbons, ketones, ethers, etc., may also be useful to dissolve some magnesium or manganese compounds or complexes. Generally, the most useful solvent will be found to be water. However, the solvent of choice for any particular Mg or Mn compound will, of course, be determined by the nature of that compound, and for that reason the foregoing list should not be considered exhaustive of all of the suitable possibilities.

Treating compounds are those which contain the elements magnesium or manganese, the two catalyst modifiers used in the present invention. Representative magnesium-containing compounds include magnesium acetate, magnesium nitrate, magnesium benzoate, magnesium propionate, magnesium 2-ethylhexanoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Representative manganese-containing compounds include manganese acetate, manganese nitrate, manganese lactate, manganese oxalate, manganese carbonate, manganese citrate, manganese tartarate, manganese bromide, manganese chloride, manganese sulfate, and manganese sulfide.

The amount of modifying metal incorporated onto the zeolite composition by reaction with these metal-containing compounds will depend upon several factors. One of these is the reaction time, i.e., the time that the ZSM-12 zeolite composition and the metal-containing source are maintained in contact with each other. With greater reaction times, all other factors being equal, a greater amount of metal is incorporated with the zeolite. Other factors upon which the amount of mangesium and maganese modifiers incorporated with the zeolite is dependent include reaction temperature, concentration of the treating compound in the reaction mixture, the degree to which the zeolite composition has been dried prior to reaction with the metal-containing compounds, the conditions of drying of the zeolite composition after reaction with the treating compounds, and the amount and type of binder incorporated with the zeolite composition.

After modifying magnesium and manganese metals have been incorporated into the zeolite composite to the extent desired, the metal containing composite can be heated subsequent to metal modification and prior to use. Such heating can be carried out in the presence of oxygen, for example, in air. Although heating may be carried out at a temperature of about 150° C., higher temperatures, e.g., up to about 500° C., are preferred. Heating is generally carried out for 1–5 hours but may be extended to 24 hours or longer. While heating temperatures above about 500° C. may be employed, they are generally not necessary. After the metal-containing composite is heated in air at elevated temperatures, it is contemplated that the modifying metals are actually present at least in part in the zeolite composite in an oxidized state, such as MgO and MnO.

The zeolite composites herein are treated with the foregoing compounds and subsequently heated, under conditions and for a time sufficient to incorporate a minor proportion of each of the modifying elements onto the zeolite composite. Generally, modifying metal oxides are incorporated to the total extent of from about 0.1% to 10% by weight of the zeolite composite, preferably from about 1% to 10% by weight of the zeolite, calculated on the basis of the elemental metals. For magnesium oxide as modifying agent, the composite can advantageously comprise from about 0.1% to about 10%, more preferably from about 0.1% to 5%, by weight of magnesium. For manganese oxide as modifying agent, the zeolite composite can advantageously comprise from about 0.1% to 10%, more preferably from about 1% to 10%, by weight manganese.

As noted, the magnesium and/or manganese-modified ZSM-12 zeolite catalysts of the present invention are especially useful for the selective conversion of methanol and/or methyl ether to a light olefin ($C_2$–$C_4$)-containing hydrocarbon product enriched in propylene. By utilizing a selected combination of a ZSM-12 zeolite catalyst along with magnesium and/or manganese catalyst modifiers, methanol conversion processes as can be realized which are more selective to propylene production than are similar processes employing other types of zeolite catalysts. Processes utilizing these particular modified ZSM-12 catalysts are also either more selective to propylene production or provide enhanced conversion of methanol-containing feed to olefins in comparison with either unmodified ZSM-12 or ZSM-12 modified with other materials. The process of the present invention, in fact, yields a light olefin-containing product wherein propylene is the major light olefin produced.

In accordance with the present process invention, a chargestock comprising methanol (methyl alcohol), methyl ether, methanol/methyl ether mixtures or mixtures of such organic materials with water can be contacted in the vapor phase with the magnesium and/or manganese modified ZSM-12 catalyst materials hereinbefore described in a reaction zone and under reaction conditions suitable for effecting conversion of methanol and/or methyl ether to olefins. Such conditions include an operating temperature between about 260° C. (~500° F.) and 540° C. (~1000° F.), preferably 400° C. and 450° C.; a pressure between about $10^4$ N/m$^2$ (0.1 atmosphere) and $3.0 \times 10^6$ N/m$^2$ (300 atmospheres) preferably $5.0 \times 10^5$ N/m$^2$ and $10^6$ N/m$^2$; and a weight hourly space velocity (WHSV) of the organic reactants between about 0.1 and 30, preferably 1 and 10. Carrier gases or diluents may be injected into the reaction zone such as, for example, hydrogen, nitrogen, helium, water, carbon monoxide, carbon dioxide, or mixtures of these gases.

When water is employed along with the organic feed, the amount of water fed with the organic charge of methanol and/or methyl ether can be generally at least about 0.25 moles of water per mole of the organic reactants. Preferably, the amount of water added can be greater than about 0.5 moles of water per mole of organic reactants. The amount of water initially added to the organic charge usually will not exceed about 40 moles per mole of said charge. Water in these amounts can generally be passed to the reaction zone with a WHSV from about 1 to 20, more preferably from about 2 to 10.

Conversion reaction conditions, including the presence or absence of diluents, can affect the selectivity of the present methanol conversion process to light olefin and propylene production as well as percent conversion of organic reactants to hydrocarbon product. However, it has been discovered that for a given set of reaction conditions the magnesium and/or manganese-modified ZSM-12 catalysts used in the present invention will generally provide improved methanol conversion and/or propylene selectivity in comparison with similar prior art processes employing other zeolites.

The methanol and/or methyl ether conversion process described herein may be carried out as a batch-type, semi-continuous or continuous operation utilizing a fixed, fluidized or moving bed catalyst system. A preferred embodiment entails use of a catalyst zone wherein the alcohol or ether charge optionally together with added water is passed concurrently or countercurrently through a fluidized or moving bed of particle-form catalyst. The latter after use may be conducted to a regeneration zone wherein coke is burned from the catalyst in an oxygen-containing atmosphere, e.g., air, at an elevated temperature, after which the regenerated catalyst can be recycled to the conversion zone for further contact with the methanol and/or ether containing feed.

The product stream in the process of the invention contains steam and a hydrocarbon mixture of paraffins and olefins, substantially devoid of aromatics. As noted, the mixture is particularly rich in light olefins, and especially rich in propylene. Thus, the predominant hydrocarbon product constitutes valuable petrochemicals. The steam and hydrocarbon products may be separated from one another by methods well known in the art. In a preferred embodiment of the invention, the unconverted methanol and/or dimethyl ether, as well as at least part of the water in the product, can be recycled to the reaction zone.

The following examples will serve to illustrate the process of this invention without limiting the same.

EXAMPLE I

Preparation Of ZSM-12

Zeolite ZSM-12 useful in the present invention can be prepared in the following manner: A solution of 96.2 grams tetraethylammoniumbromide and 17.5 grams NaOH and 300 grams H$_2$O is made. Five grams of NaAl$_2$ (41.8 percent Al$_2$O$_3$) is dissolved in the solution. Five hundred grams of colloidal silica, e.g., Ludox, are added to the solution and mixed for 15 minutes. The resulting mixture is crystallized in a polypropylene jar without agitation for 84 days at 100° C. The product analysis by X-ray diffraction is ZSM-12 material with a SiO$_2$/Al$_2$O$_3$ ratio of 82. The product is washed and dried at 110° C. The dried powder is pre-calcined for 3 hours at 370° C. in air and then cooled to room temperature in a dessicator. This is followed by four contacts each with 10 ml. of 5 percent NH$_4$Cl/gram of calcined powder at 90° C. for 1 hour. Each contact is made with stirring. The product is washed free of Cl$^-$ ions at room temperature and then dried at 110° C. The sodium content of the zeolite at this stage is less than 0.01 percent. The dried powder can then be calcined by heating it in air at 538° C. for 10 hours. The product can then be cooled in a dessicator.

Zeolite ZSM-12 made in this general manner can be synthesized with various silica to alumina ratios and can be pretreated, e.g. by steaming, to produce zeolites of various alpha values.

EXAMPLE II

Mg/Mn Modification of ZSM-12

ZSM-12 samples, prepared in the general manner described in Example I, are modified in their ammonium exchanged form to incorporate both magnesium and manganese therein. Composites of NH$_4$-ZSM-12 in 35% alumina binder are washed two times with an aqueous solution which is 1M Mn(OAc)$_2$ and 0.2M Mg (OAc)$_2$. Contact with such solution is made for two hours at reflux, followed by water washes, drying and calcination in air at 500° C. Samples prepared in this manner generally contain about 4.2% Mn and 0.5% Mg by weight. Catalyst samples containing only magnesium and catalyst samples containing only manganese are also made in similar manner using either a 1M solution of magnesium acetate or a 1M solution of manganese acetate to treat the zeolite. Mg-modified zeolites prepared in this manner contain about 3.0% Mg by weight. Mn-modified zeolites prepared in this manner contain about 3.9% Mn by weight.

EXAMPLE III

Effect of Cation and Short Term Aging On Methanol Conversion Over ZSM-12

Using catalyst samples prepared in the general manner of Examples I and II, methanol/water mixtures are catalytically converted to hydrocarbons and the resulting hydrocarbon products are analyzed. In such a procedure, a fixed bed, down-flow quartz reactor with a central thermowell is used for atmospheric pressure runs. Liquids are fed with a syringe pump. Gas is metered with a manual low flow controller. A ⅜" stainless steel reactor with central thermowell is used in the down-flow mode for pressure runs. 1.5 grams of catalyst are used in the reactors and products are collected for one hour periods. Gases are measured in a dry gas tower with a mercury-sealed float, and analyzed on a silica gel column with a thermoconductivity detector. Liquids are condensed with ice water cooling. Methanol/dimethyl ether conversions are calculated on a carbon molar basis (approximately equivalent to a $CH_2$ basis).

Methanol conversion runs were made using several types of ZSM-12 zeolite catalysts. Catalyst description, reaction conditions and methanol conversion results are set forth in Table I.

TABLE I

Methanol Conversion Over ZSM-12
Effect of Cation and Short Term Aging Effects

| Run No. | 1 | 2 | 3 | 4 | 5 |
|---|---|---|---|---|---|
| Catalyst | HZSM-12 | HZSM-12 | MgZSM-12 | Mn—ZSM-12 | Mg/Mn-ZSM-12 |
| $SiO_2:Al_2O_3/\alpha$ | (180/103) | (180/103) | (180/20) | (180/-) | (180/13) |
| WHSV MeOH | 2.1 | 2.1 | 2.1 | 2.1 | 2.1 |
| $H_2O$ | 3.5 | 3.5 | 3.5 | 3.5 | 3.5 |
| Temperature (°C.) | 390 | 450 | 450 | 450 | 450 |
| Time on Stream (hrs.) | — | — | — | — | 2 |
| Conversion to Hydrocarbons (C Mol. %) | 97.3 | 99.5 | 80.5 | 93 | 91.9 |
| Selectivity to Hydrocarbons (Wt. %) | | | | | |
| COX | 0.1 | 0.1 | 0.1 | 0 | 0 |
| $C_1$ | 0.4 | 0.5 | 0.4 | 0.4 | 0.5 |
| $C_2°$ | 0.1 | 0.1 | 0.1 | 0.1 | 0.1 |
| $C_2=$ | 3.2 | 6.4 | 3.1 | 3.5 | 3.8 |
| $C_3°$ | 5.2 | 5.4 | 1.5 | 2.4 | 2.5 |
| $C_3=$ | 20.0 | 35.1 | 48.3 | 42.0 | 59.5 |
| $C_4°$ | 18.6 | 13.5 | 4.6 | 7.9 | 6.1 |
| $C_4=$ | 16.2 | 20.9 | 17.6 | 17.8 | 16.9 |
| $C_5$ | 2.0 | 3.4 | 10.4 | 13.6 | 1.2 |
| $C_6$ | 0 | 0.2 | 0.9 | 1.6 | 0 |
| liquid | 34.3 | 14.4 | 12.9 | 10.6 | 9.6 |
| $C_2$—$C_4=$ | 39.4 | 62.4 | 69.0 | 63.3 | 80.2 |

The Table I data demonstrate that methanol conversion over a ZSM-12 zeolite catalyst modified by incorporation of both magnesium and manganese is especially selective to light olefin production with the major light olefin product being propylene. It will be understood that the symbol, $\alpha$, as used in Table I, stands for the alpha value of the catalyst. As pointed out previously in this specification, alpha value is a measure of the catalytic cracking activity of a catalyst. Accordingly, for example, it will be understood that the catalyst of Run No. 1 has a silica to alumina ratio (i.e. $SiO_2:Al_2O_3$) of 180 and an alpha value ($\alpha$) of 130.

EXAMPLE IV

Effect of Temperature on Methanol Conversion Over ZSM-12

Using the general testing procedures described in Example III, additional conversion runs are made at various reaction temperatures using the Mg/Mn-ZSM-12 zeolite sample employed in Example III. Reaction conditions and conversion results are set forth in Table II.

TABLE II

Methanol Conversion Over Mg/Mn—ZSM-12
Effect of Temperature

| Run No. | 1 | 2 | 3 | 4 | 5 | 6 |
|---|---|---|---|---|---|---|
| WHSV | | | | | | |
| MeOH | 2.1 | 2.1 | 2.1 | 2.1 | 2.1 | 2.1 |
| $H_2O$ | 3.5 | 3.5 | 3.5 | 3.5 | 3.5 | 3.5 |
| Temperature (°C.) | 350 | 370 | 390 | 420 | 450 | 475 |
| Conversion to Hydrocarbons (C mol. %) | 32.9 | 43.3 | 65.5 | 90.0 | 99.2 | 100 |
| Selectivity to Hydrocarbons (Wt %) | | | | | | |
| COX | 0 | 0 | 0 | 0 | 0 | 0 |
| $C_1$ | 0.5 | 0.5 | 0.4 | 0.3 | 0.4 | 0.5 |
| $C_2°$ | 0 | 0 | 0 | 0 | 0.1 | 0.1 |
| $C_2=$ | 0.7 | 0.7 | 1.1 | 2.1 | 3.7 | 5.3 |
| $C_3°$ | 1.1 | 1.0 | 1.4 | 1.8 | 2.1 | 2.1 |
| $C_3=$ | 39.3 | 34.5 | 40.2 | 45.4 | 49.6 | 52.1 |
| $C_4°$ | 10.4 | 9.0 | 9.5 | 7.9 | 5.8 | 4.7 |
| $C_4=$ | 18.7 | 20.5 | 19.0 | 19.0 | 18.3 | 18.6 |
| $C_5$ | 16.4 | 13.7 | 13.9 | 12.8 | 11.8 | 11.4 |
| $C_6$ | 1.4 | 1.5 | 1.8 | 1.7 | 1.5 | 1.4 |
| liquid | 11.4 | 18.4 | 12.8 | 8.7 | 6.6 | 3.6 |
| $C_2$-$C_4=$ | 58.8 | 55.8 | 60.3 | 66.5 | 71.6 | 76.0 |

The Table II data demonstrate that, at higher temperatures, Mg/Mn-ZSM-12 promotes greater conversion of methanol to hydrocarbon with generally higher selectivity to production of $C_2$–$C_4$ olefins. Propylene is the major light olefin product at all of the exemplified temperatures.

EXAMPLE V

Effect of Reactant Dilution on Methanol Conversion Over ZSM-12

Using the general testing procedures described in Example III, additional methanol conversion runs are made over Mg/Mn-ZSM-12 using different temperatures, different space velocities for methanol and water and, in one instance, using a nitrogen diluent. Reaction conditions and conversion results are set forth in Table III.

TABLE III

Methanol Conversion Over Mg/Mn—ZSM-12
Effect of Dilution

| Run No. | 1 | 2 | 3 | 4 | 5 |
|---|---|---|---|---|---|
| WHSV | | | | | |
| MeOH | 2.2 | 2.1 | 2.1 | 2.2 | 2.2 |
| $H_2O$ | — | 3.5 | 3.5 | 6.2 | — |
| $N_2$ | — | — | — | — | 2.8 |
| Temperature (°C.) | 362 | 362 | 450 | 460 | 450 |
| Conversion to Hydrocarbons (C mol. %) | 64.6 | 19.9 | 99.2 | 99.2 | 98.6 |
| Selectivity to Hydrocarbons (Wt %) | | | | | |
| COX | — | — | 0 | 0 | 0 |
| $C_1$ | 0.6 | 0 | 0.4 | 0.4 | 0.7 |
| $C_2°$ | 0 | 0 | 0.1 | 0 | 0 |
| $C_2=$ | 1.6 | 1.0 | 3.7 | 3.6 | 1.5 |
| $C_3°$ | 1.3 | 0.9 | 2.1 | 1.3 | 1.4 |
| $C_3=$ | 17.1 | 28.7 | 49.6 | 55.1 | 44.4 |
| $C_4°$ | 14.5 | 7.8 | 5.8 | 3.8 | 7.3 |
| $C_4=$ | 15.2 | 26.0 | 18.3 | 18.9 | 22.0 |
| $C_5$ | 28.9 | 25.8 | 11.8 | 11.3 | 18.6 |
| $C_6$ | 28.9 | 25.8 | 1.5 | 1.8 | 2.0 |
| liquid | 20.5 | 9 | 6.6 | 3.6 | 0 |
| $C_2-C_4=$ | 34.2 | 55.7 | 71.6 | 77.6 | 67.9 |

The Table III data again demonstrate the selectivity to light olefins in general and to propylene in particular for methanol conversion runs over Mg/Mn-ZSM-12.

EXAMPLE VI

Comparison of ZSM-12 with ZSM-5 in Methanol Conversions

ZSM-12 and ZSM-5 catalysts were prepared in substantially the same manner as described in Example II. More particularly, the zeolites of these catalysts had approximately the same silica to alumina ratio ($SiO_2$:$Al_2O_3$ = 260-290) and were ion exchanged at 90° C. with a solution that was 0.2M Mg(OAc)$_2$ and 1.0M Mn(OAc)$_2$, followed by water washes, drying and calcination at 500° C.

Methanol conversion runs were made using these ZSM-12 and ZSM-5 catalysts. Reaction conditions and methanol conversion results with the Mg/Mn-ZSM-5 catalyst are set forth in Table IV. Reaction conditions and methanol conversion results with the Mg/Mn-ZSM-12 catalyst are set forth in Table V.

TABLE IV

Methanol Conversion Over Mg/Mn—ZSM-5

| Run No. | 1 | 2 | 3 |
|---|---|---|---|
| WHSV | | | |
| MeOH | 2.3 | 2.3 | 2.3 |
| $H_2O$ | 3.9 | 3.9 | 3.9 |
| Temperature (°C.) | 450° | 500° | 550° |
| Conv. wt. % | 92 | 100 | 100 |
| Wt % sel. in HC | | | |
| $C_2=$ | 4.0 | 7.8 | 11.5 |
| $C_3=$ | 36.9 | 47.4 | 41.7 |
| $C_4=$ | 22.8 | 25.7 | 19.5 |
| $C_1-C_4°$ | 4.9 | 3.8 | 3.1 |
| $C_5+$ | 31.5 | 15.8 | 24.2 |
| $C_3=/C_2=$ | 9.2 | 6.1 | 3.6 |

TABLE V

Methanol Conversion Over Mg/Mn—ZSM-12

| Run No. | 1 | 2 | 3 |
|---|---|---|---|
| WHSV | | | |
| MeOH | 2.4 | 2.4 | 2.4 |
| $H_2O$ | 4.0 | 4.0 | 4.0 |
| Temperature (°C.) | 450° | 500° | 550° |
| Conv. wt. % | 99 | 100 | 100 |
| wt % sel. in HC | | | |
| $C_2=$ | 2.4 | 4.8 | 8.5 |
| $C_3=$ | 40.7 | 48.9 | 53.3 |
| $C_4=$ | 28.3 | 27.4 | 24.2 |
| $C_1-C_4°$ | 9.5 | 7.2 | 5.1 |
| $C_5+$ | 19.1 | 11.6 | 8.9 |
| $C_3=/C_2=$ | 17.0 | 10.1 | 6.3 |

A comparison of the results shown in Tables IV and V show that, under comparable conditions, the ZSM-12 catalyst gave higher propylene yields than the ZSM-5 catalyst.

What is claimed is:

1. A process for converting a methanol-containing feed to an olefin-containing hydrocarbon product having a propylene:ethylene weight ratio of at least 35.1:6.4, said process comprising contacting said methanol-containing feed in a reaction zone under methanol conversion conditions with a ZSM-12 zeolite catalyst modified by incorporation thereinto of a minor amount of a modifier selected from magnesium oxide, manganese oxide and a combination of both magnesium oxide and manganese oxide.

2. A process according to claim 1 wherein said catalyst contains from about 0.1% to 10% by weight magnesium, calculated on the basis of the elemental metal.

3. A process according to claim 1 wherein said catalyst contains from about 0.1% to 10% by weight manganese, calculated on the basis of the elemental metal.

4. A process according to claim 1 wherein said catalyst contains from about 0.1% to 10% by weight magnesium and from about 0.1% to 10% by weight manganese, calculated on the basis of the elemental metals.

5. A process according to claim 1 wherein said methanol conversion conditions include a reaction temperature of from about 400° C. to 450° C. and a pressure of from about $5 \times 10^5$ $N/m^2$ to $10^6$ $N/m^2$.

6. A process according to claim 1 wherein said methanol conversion conditions include a weight hourly space velocity for the organic reactants of the methanol-containing feed of from about 0.1 to 30.

7. A process according to claim 1 wherein water is cofed to the reaction zone in an amount of from about 1 to 20 moles of water per mole of organic reactants.

8. A process according to claim 7 wherein the weight hourly space velocity of water co-fed to the reaction zone ranges from about 1 to 20.

9. A process according to claim 1 wherein said catalyst further comprises a binder for said zeolite.

10. A process according to claim 1 wherein said weight ratio of propylene:ethylene is no greater than 39.3:0.7.

11. A process according to claim 1 wherein said magnesium of said magnesium oxide and/or said manganese of said manganese oxide constitute the only modifying metals incorporated into said ZSM-12 zeolite catalyst.

12. A process according to claim 1 wherein said weight ratio of propylene:ethylene is at least 52.1:5.3.

13. A process for converting a methanol-containing feed to an olefin-containing hydrocarbon product having a propylene:ethylene weight ratio of at least 35.1:6.4, said process comprising contacting said methanol-containing feed in a reaction zone under methanol conversion conditions with a ZSM-12 zeolite catalyst.

* * * * *

UNITED STATES PATENT AND TRADEMARK OFFICE
CERTIFICATE OF CORRECTION

PATENT NO. : 4,665,268

DATED : May 12, 1987

INVENTOR(S) : Carol S. Lee and George E. Stead

It is certified that error appears in the above-identified patent and that said Letters Patent is hereby corrected as shown below:

Col. 1, line 24, "toime" should be --time--.

Col. 1, line 35, "catalysts" should be --catalyst--.

Col. 1, line 46, "selectively" should be --selectivity--.

Col. 1, line 67, "process" should be --processes--.

Col. 2, lines 14-15, "product" should be --production--.

Col. 2, line 51, "reaction" should be --reactant--.

Col. 2, line 58, "30 wt %" should be --20 wt %--.

Col. 4, line 61, "hour" should read --hourly--.

Col. 5, line 54, before "select" insert --so--.

Col. 6, line 11, "3,832,499" should read --3,832,449--.

Col. 6, line 31, "calls" should read --class--.

Col. 8, line 55, "from" should read --form--.

Signed and Sealed this

Twenty-fourth Day of November, 1987

Attest:

DONALD J. QUIGG

*Attesting Officer*    *Commissioner of Patents and Trademarks*